United States Patent [19]
Bryan et al.

[11] Patent Number: 5,116,741
[45] Date of Patent: May 26, 1992

[54] BIOSYNTHETIC USES OF THERMOSTABLE PROTEASES

[75] Inventors: Philip N. Bryan, Silver Spring; Michael W. Pantoliano, Germantown; Michele L. Rollence, Damascus, all of Md.; Chi H. Wong, College Station, Tex.

[73] Assignee: Genex Corporation, Gaithersburg, Md.

[21] Appl. No.: 301,683

[22] Filed: Jan. 26, 1989

Related U.S. Application Data

[63] Continuation-in-part of Ser. No. 180,756, Apr. 12, 1988, Pat. No. 4,990,452, which is a continuation-in-part of Ser. No. 180,757, Apr. 12, 1988, which is a continuation-in-part of Ser. No. 34,964, Apr. 6, 1987, Pat. No. 4,908,773, and a continuation-in-part of Ser. No. 34,965, Apr. 16, 1987, abandoned, which is a continuation-in-part of Ser. No. 828,545, Feb. 12, 1986, abandoned.

[51] Int. Cl.$^5$ .................. C12P 19/38; C12P 19/40
[52] U.S. Cl. ........................................ 435/87; 435/88
[58] Field of Search ............ 435/68, 70, 71, 72, 435/91, 171.1, 172.3, 221; 44, 45, 69, 135, 41, 88, 87; 536/24, 26

[56] References Cited

U.S. PATENT DOCUMENTS

| | | | |
|---|---|---|---|
| 3,770,587 | 11/1973 | Hamsher et al. | 195/63 |
| 3,838,009 | 9/1974 | Fukumoto et al. | 195/65 |
| 3,869,349 | 3/1975 | Goodhue et al. | 195/103.5 |
| 4,086,136 | 4/1978 | Isowa | 195/29 |
| 4,293,648 | 10/1981 | Davino | 435/70 |
| 4,386,160 | 5/1983 | Branner-Jorgensen | 435/221 |
| 4,760,025 | 7/1988 | Estell et al. | 435/222 |
| 4,800,162 | 1/1989 | Matson | 435/280 |
| 4,914,031 | 4/1990 | Zukowski et al. | 435/222 |

FOREIGN PATENT DOCUMENTS 272564 6/1986 European Pat. Off. .

OTHER PUBLICATIONS

Klibanov, A. M., *Chemtech.* 16:354-359 (1986).
Zaks, A., et al., *J. Biol. Chem.* 263:3194-3201 (1988).
Riva, S. et al., *J. Am. Chem. Soc.*, 110:584-589 (1988).
Margolin, A. L., et al., *J. Am. Chem. Soc.* 109:7885-7887 7887 (1987).
Fruton, J. S., *Adv. Enzymol.* 53:239-306 (1982).
Chaiken, I. M. et al., *Appl. Biochem. Biotechnol.* 7:385-389 (1982).
Barbas, C. F. et al., *J. Am. Chem. Soc.* 110:5162-5166 (1988).
Neet, K. E. et al., *Proc. Natl. Acad. Sci. USA* 56:1606-1611 (1966).
Nakatsuka, T. et al., *J. Am. Chem. Soc.* 109:3808-3810 (1987).
Vasantha, N. et al., *J. Bact.* 159:811-819 (1984).
Wells, J. A. et al., *Nucl. Acids Res.* 11:7911-7925 (1983).
Bryan, P. N. et al., *Proc. Natl. Acad. Sci. USA* 83:3743-3745 (1986).
Jacobs, M. et al., *Nucl. Acids Res.* 13:8913-8926 (1985).
Nedkov, P., et al., *Biol. Chem. Hoppe-Seyler* 366:421-430 (1985).
Kurihara, M., et al., *J. Biol. Chem.* 247:5619-5631.
Svendsen, I., et al., *FEBS Lett.* 196:228-232 (1986).
Meloun, B., et al., *FEBS Lett.* 183:195-200 (1985).
Jany, K.-D., et al., *Biol. Chem. Hoppe-Seyler* 366:485-492 (1985).
Gerlt, J. A., *Chem. Rev.* 87:1079-1105 (1987).
Bryan, P. N., *Biotech. Adv.* 5:221-234 (1987).

(List continued on text page.)

*Primary Examiner*—Richard A. Schwartz
*Attorney, Agent, or Firm*—Sterne, Kessler, Goldstein & Fox

[57] ABSTRACT

The invention relates to the novel use of mutants of subtilisin in organic syntheses reactions in non-native environments. Especially the invention relates to methods for the use of mutant subtilisins in organic solvents for the catalysis of reactions involving ester formation and cleavage, including acylations and deacylations, and amidations and deamidations. The methods provide novel strategies which are useful in the synthesis of deoxynucleosides, dideoxynucleosides, peptides, sugars and the like.

3 Claims, 3 Drawing Sheets

OTHER PUBLICATIONS

Bryan, P. N., et al., *Proteins, Structure, and Genetics* 1:326–334 (1986).
Pantoliano, M. W., et al., *Biochemistry* 26:2077–2082 (1987).
Estell, D. A., et al., *J. Biol. Chem.* 260:6518–6521 (1985).
Wells, J. A. et al., *Philos. Trans. R. Soc. London A* 317:415–423 (1986).
Estell, D. A., et al., *Science* 233:659–663 (1986).
Wells, J. A., et al., *Proc. Natl. Acad. Sci. USA* 84:1219–1223 (1987).
Pantoliano, M. W., et al., *Biochemistry* 27:8311–8317 (1988).
Cunningham B. C., et al., *Prot. Engin.* 1:319–325 (1987).
Estell, D. A., et al., *World Biotech. Rep.* 2:181–187 (1984).
Kamaike, K., et al., *Nucleic Acids. Res. Symp.* Series No. 16, IRL Press, Oxford, pp. 177–180 (1985).
Liguori, A., et al., *Tetrahedron* 44:229–234 (1988).
Mitsunobu, O., et al., *Chem. Soc. Jpn.* 45:245–247 (1972).
Shimokawa, S., et al., *Chem. Soc. Jpn.* 49:3357–3358 (1976).
Ishido, Y. et al., *J. Chem. Soc.* (Perkins Trans. I) 2088–2098 (1979).
Prisbe, E. J., et al., *Synth. Commun.* 15:401–409 (1985).
Pfitzner, K. E., et al., *J. Org. Chem.* 29:1508–1511 (1964).
McCarthy, J. R., et al., *J. Am. Chem. Soc.* 88:1549–1553 (1966).
Michelson, A. M., et al., *J. Chem. Soc.* 816–823 (1955).
Horwitz, J. P. et al., *J. Org. Chem.* 32:817–818 (1967).
Samukov, V. V. et al., *Bioorg. Khim.* 9:52–59 (1983).
Mitzuno, Y., et al., *J. Org. Chem.* 40:1385–1390 (1975).
Beaucage, S. L., et al., *Tetrahedron Lett.* 22:1859–1862 (1981).
Abstract of European Patent Application No. 357009.
Wang et al., *J. Amer. Chem. Soc. 110:* 7200–7205 (1988).
Hirono, S. et al. 1984 *J. Mol. Biol.* 179:389–413.
Carter & Wells 1988 (Apr. 7) *Nature* 332:564–568.
Arnold, F. H., *Protein Engineering* 2:21–25 (1988).
Arnold, F. H., *Tibtech* 8:244–249 (1990).

BIOSYNTHETIC USES OF THERMOSTABLE PROTEASES

CROSS REFERENCE TO RELATED APPLICATIONS

This application is a continuation-in-part application of pending U.S. Ser. No. 07/180,756, filed Apr. 12, 1988, now U.S. Pat. No. 4,990,452, which is a continuation-in-part application of pending U.S. Ser. No. 07/180,757, filed Apr. 12, 1988, which is a continuation-in-part of U.S. Ser. No. 07/034,964, filed Apr. 6, 1987, now U.S. Pat. No. 4,908,773, and which is also a continuation-in-part of U.S. Ser. No. 07/034,965, filed Apr. 6, 1987, now abandoned, both applications being continuation-in-part applications of U.S. Ser. No. 06/828,545, filed Feb. 12, 1986, now abandoned, the contents of each are fully incorporated herein by reference.

FIELD OF THE INVENTION

The invention pertains to the use of mutant subtilisin enzymes as biological catalysts in organic syntheses in non-native environments. The invention further relates to the use of mutant subtilisin enzymes in organic solvents for the catalysis of reactions involving ester formation and cleavage, including acylations and deacylations, and amidations and deamidations. The methods of invention provide novel strategies which are useful in the synthesis of deoxynucleosides, dideoxynucleosides, peptides, sugars and the like.

BACKGROUND OF THE INVENTION

Inherent properties of a naturally occurring or "wild type" enzyme are not necessarily optimized for catalytic utilization of the enzyme outside of the native biological environment. Use of the isolated enzyme in non-native non-biological environments is often limited by such properties as the enzyme's substrate specificity, thermostability, activity levels under various conditions (e.g., temperature and pH), oxidation stability, and the like. It may thus be desirable to alter a natural property of an enzyme to optimize a certain characteristic of the enzyme for a specific use, or for use in a specific non-native non-biological environment (Klibanov, A.M., Chemtech 16:354 (1986); Zaks, A. et al., J. Biol. Chem. 263:3194 (1988)).

Enzymatic catalysts have been much desired in the area of organic syntheses, especially, acylation reactions, for example, in the in vitro chemical synthesis of nucleosides and peptides, and in the resolution of chiral alcohols and acids, and the incorporation of D-amino acids into peptides. However, enzymatic catalysts are not generally useful in organic syntheses because of the catalytic instability of natural enzymes in many of the relatively harsh reaction environments routinely used to drive the syntheses reactions, such as high concentrations or organic solvents and/or high temperatures.

One area where an enzymatic catalyst is greatly desired is in those organic syntheses which involve selective acylation reactions such as those which occur in the regioselective acylation of sugars and nucleosides. Selective chemical acylations of nucleosides have been reported in only a few cases (Brown, D. M. et al., J. Chem. Soc. K. et al., Nucleic Acids Res. Symposium Series No. 16, IRL Press, Oxford, pp. 177-180 (1985); Liguori, A. et al., Tetrahedron 44:229-234 (1988); Mitsunobu, O. et al., Chem. Soc. Jpn. 45:245 (1972); Shimokawa, S. et al., Chem. Soc. Jpn. 49:3357-3358 (1976)). Previously, to selectively acetylate the more reactive 2'-hydroxyl positions, the amount of acylating agent employed was limited (Kamaike, K. et al. (Nucleic Acids Res. Symposium Series No. 16, IRL Press, Oxford, pp. 177-180 (1985)). Liguori, et al. (Tetrahedron 44:229-234 (1988)) recently reported the selective acylation of certain 2'-deoxynucleosides by use of a highly hindered mixed anhydride. Regioselective formation of the 5'-0-acyl groups have been accomplished by in situ displacement of an activated 5'-hydroxyl derivative (Mitsunobu, O. et al., Chem. Soc. Jpn. 45:245 (1972); Shimokawa, S. et al., Ibid 49:3357-3358 (1976)). This last procedure allows distinct time savings to be achieved over the traditional three step approach (Brown, D. M. et al., J. Chem. Soc. 3299 (1950)) but is not an acylation reaction in the formal sense.

Other methods involving selective deacylation of fully blocked nucleosides have also been used to prepare the 5'-0-acylnucleosides (Ihido, Y. et al., J. chem. Soc. (Perkin Trans. I) 2088 (1979)). Regioselective enzymatic acylations of certain nucleosides have recently been accomplished using subtilisin Carlsberg (Riva, S. et al., J. Am. Chem. Soc. 110:584-589 (1988)) with moderate to good efficiency. The utility of a recently reported efficient deoxygenation (Prisbe, E. J. et al., Synth. Commun. 15:401-409 (1985)) leading to synthesis of the AIDS virus (HIV) inhibiting 2',3'-dideoxynucleosides (Mitsuya, H. et al., Proc. Nat'l. Acad. Sci. USA 83:1911 (1986)) suffered from the losses associated with preparing the starting materials, the 5'-0-acetyl-2-deoxynucleosides. For example, 5'-0-acetylthymidine was obtained from thymidine in approximately 50% yield over two steps (Ihido, Y. et al., J. Chem. Soc. (Perkin Trans. I) 2088 (1979). Methods for the efficient synthesis of the 2',3'-dideoxynucleosides are highly desirable as 2',3'-dideoxynucleosides, especially 2',3'-dideoxyadenosine and 2',3'-dideoxyinosine, have utility as antiviral agents, including anti-HIV activity (Mitsuya, H. et al., Proc. Natl. Acad. Sci. USA 83:1911-1915 (1986), and as reagents for DNA sequencing (Sanger, F. et al., Proc. Natl. Acad. Sci. USA 74:5463 (1977). Existing methods for the preparation of these nucleosides are tedious and result in a low yield (Pfitzner, K. E. et al., J. Org. Chem. 29:1508 (1964); McCarthy, J. R. et al., J. Am. Chem. Soc. 88:1549 (1966); Michelson, A. M., et al., J. Chem. Soc., 816 (1955); Horwitz, J. P., et al., J. Org. Chem. 32:817 (1967); and Samukov, V. V. et al., Bioorg. Khim. 9:132 (1983)). Thus a need exists for a method of synthesizing precursors to biomedically important nucleosides in an efficient and specific manner.

Another area where an enzymatic catalyst is greatly desired is in peptide synthesis. The possibility of using proteases to catalyze the formation of a peptide bond rather than the hydrolysis and cleavage of a peptide bond was first discussed by van't Hoff, J. H. et al., Chem. 18:1 (1898), and experimentally demonstrated by Bergmann, M. et al., J. Biol. Chem. 124:1 (1938). However, although the idea of using proteases in organic peptide syntheses as peptide ligases has been widely examined and desired (Margolin, A. L. et al., J. Am. Chem. Soc., 109:7885-7887 (1987); Fruton, J.S., Adv. Enzymol. 53:239-306 (1982); Chaiken, I. M. et al., Appl. Biochem. Biotechnol. 7:385-399 (1982); Jakubke, H.-D. et al., Angew. Chem. Int. Ed. Engl. 24:85-93 (1985); and Kullman, W., Enzymatic Peptide Synthesis, CRC Press, Boca Raton, Flor. (1987)), the application of proteases to peptide syntheses has been limited by the lack of a protease which is catalytically stable in the reaction environments required for in vitro amino acid or peptide ligation and synthesis.

A subtilisin is a serine protease naturally produced by Gram positive bacteria and by fungi. A serine protease is an endoprotease which catalyzes the hydrolysis of a peptide bond in which there is an essential serine residue at the active site. Serine proteases can be inhibited by phenylmethanesulfonylfluoride and by diisopropyl fluorophosphate.

The use of native bacterial subtilisin to catalyze peptide bond formation in the presence of a water-miscible solvent is known (Barbas, C.F. et al., *J. Am. Chem. Soc.* 110:5162-5166 (1988); West, J. B. et al., *J. Am. Chem. Soc.* 110:3709 (1988); Margolin, A. L. et al., *J. Am. Chem. Soc.* 109:7885-7887 (1987); and Gross, A. T., European Patent Application Publication No. 272,564.) Bacterial subtilisin has been reported to be active in a number of anhydrous organic solvents, including tert-amyl alcohol, tetrahydrofuran (THF), acetone, acetonitrile, ethyl acetate and dioxane. It is also known that subtilisin catalyzes the formation of a peptide bond between an N-protected amino acid chloroethyl ester and an amino acid amide. However, the native subtilisin enzyme is unable to catalyze peptide bond formation when it is used in an environment comprising an aqueous solution containing 40% N,N-dimethylformamide (DMF) at either pH 7 or pH 10, an environment often desired in organic syntheses.

Thiolsubtilisin is a chemically altered derivative of native subtilisin (Neet, K.E. et al., *Proc. Nat'l Acad. Sci. USA* 56:1606 (1966), and Philipp, M. et al., *Mol. Cell Biochem.* 51:5 (1983)). Thiolsubtilisin is a very poor protease but retains the ability to catalyze the reverse reaction, that of peptide ligation, and hence is able to catalyze the formation of a peptide bond. The use of thiolsubtilisin as a catalyst for peptide condensation has been disclosed (Nakatsuka, T. et al., *J. Am. Chem. Soc.* 109:3808-3810 (1987)). Thiolsubtilisin was found to be too inactive or too slow in anhydrous DMF to be used for preparative peptide synthesis. However a high-yield of peptide bond formation was achieved in aqueous DMF (50% water v/v).

The subtilisin gene from *Bacillus amyloliquefaciens* (subtilisin BPN') has been cloned and expressed at high levels from its natural promoter sequences in *Bacillus subtilis* (Vasantha, N. et al., *J. Bact.* 159:811 (1984); Wells, J. A. et al., *Nucleic Acid Res.* 11:7911 (1983)). This has enabled the introduction of mutations in vitro into the plasmid-encoded subtilisin gene and allowed the analysis of the effect of those mutations on the properties of the altered enzyme. Mutant subtilisin genes have been cloned into a strain of *B. subtilis* which contains a chromosomal deletion of its subtilisin gene and therefore produces no background wild type activity. Most mutant enzymes are efficiently expressed from this vector and are secreted into the culture medium at a concentration of about 1 g/L. Subtilisin is the major secreted protein in this system and comprises almost 80% of the total extracellular protein (Bryan, P. N. et al., *Proc. Natl. Acad. Sci. USA* 83:3743 (1986)).

The amino acid sequences of at least six subtilisins are known. These include five subtilisins from Bacillus strains (subtilisin BPN', subtilisin Carlsberg, subtilisin DY, subtilisin amylosaccharticus, and mesenticopeptidase) (Vasantha, N. et al., *J. Bacteriol.* 159:811-819 (1984); Jacobs et al., *Nucleic Acids Res.* 13:8913-8926 (1985); Nedkov et al., *Biol. Chem. Hoppe-Seyler* 366:421-430 (1985); Kurihara et al., *J. Biol. Chem.* 247:5619-5631 (1972); and Svendsen et al., FEBS Lett. 196:228-232 (1986) and the subtilisin thermitase from *Thermoactinomyces vulgaris* (Meloun et al., FEBS Lett. 183:195-200 (1985)).

The amino acid sequences from two fungal proteases which are closely related to subtilisin BPN' are also known: proteinase K from *Tritirachium album* (Jany et al., *Biol. Chem. Hoppe-Seyler* 366:485-492 (1985)) and thermomycolase from the thermophilic fungus, *Malbranchea pulchella* (Gaucher et al., *Methods Enzymol.* 45:415-433 (1976)). These enzymes have been shown to be related to subtilisin BPN', not only through their primary sequences and enzymological properties, but also by comparison of x-ray crystallographic data. (McPhalen et al., FEBS Lett. 188:55-58 (1985); and Pahler et al., *EMBO J.* 3:1311-1314 (1984)).

Through the techniques of site specific mutagenesis nearly any amino acid position in a target protein can be manipulated at will (Smith, M., *Ann. Rev. Genet.* 19:423 (1985)). Much of the past efforts in this field have been directed at elucidation and manipulation of the active site regions of various enzymes (Gerlt, J. A., *Chem. Rev.* 87:1079 (1987)). Site specific mutagenesis has served as a means of creating proteins with improved characteristics for specific industrial and therapeutic uses (Bryan, P. N., *Biotechnology Advances* 5:221 (1987)). Reported modifications of the subtilisin gene have been directed to increasing the thermostability of the enzyme (Bryan, P.N. et al., *Proteins: Structure, and Genetics* 1:326; (1986); Pantoliano, M. W. et al., *Biochemistry* 26:2077 (1987); Estell, D. A. et al., *J. Biol. Chem.* 260:6518 (1985); Bryan, P. et al., *Proc. Nat'l. Acad. Sci. USA* 83:3743 (1986); Wells, J. A. et al., *Philos. Trans. R. Soc. London A* 317:415 (1986); Estell, D. A. et al., *Science* 233:659 (1986); Well, J. A. et al., *Proc. Nat'l Acad. Sci. USA* 84:1219 (1987)). An enzyme more stable to oxidative environments was produced by replacement of an oxidatively Tabile methionine residue (Estell, D. A. et al., *J. Biol. Chem.* 260:6518 (1985)). The inclusion of a disulfide bridge between residues 22 and 87 contributed approximately 1.3 kcal/mol to the free energy of unfolding (Pantoliano, M. W. et al., *Biochemistry* 26:2077 (1987)). This is significant since the total energy of unfolding for most proteins is only 5-15 kcal/mol (Creighton, T. E., *Proteins: Structure and Molecular Properties* W. H. Freeman, New York (1984)). Improvement of certain hydrogen-bonding interactions by a single point mutation increased the half-life of thermal inactivation four-fold over the native enzyme (Bryan, P. N. et al., *Proteins: Structure, and Genetics* 1:326 (1986)).

However, none of the prior art recognized that subtilisins which have been mutated to be more stable at higher temperatures may also possess new, unobvious advantages which make them highly useful in organic syntheses in the presence of organic solvents. Thus there remains a need for a catalytically stable enzyme catalyst capable of catalyzing chemical reactions in non-native organic environments in an efficient manner suitable for the bulk production of the product.

SUMMARY OF THE INVENTION

The invention relates to novel uses of mutant subtilisin enzymes which are unexpected and increased enzymatic stability in non-native organic environments. Especially, the invention relates to the use of mutant subtilisin enzymes for the formation and cleavage of amide and ester bonds in organic syntheses.

DEFINITIONS

By "peptide bond" is meant an amide linkage between the α-carboxyl and α-amino functions of adjacent amino acids.

By "non-native environment" is meant a reaction condition which includes a parameter not usually encountered by the native (wild type) enzyme in its in vivo environment or milieu. Examples of such parameters include organic solvents and/or temperature or pH extremes.

By "enzymatic stability" is meant the retention of a specific catalytic activity inherent to the enzyme under certain defined conditions.

By the "formation" of an amide bond is meant the condensation of a carboxy-containing molecule with a primary or secondary amino compound with elimination of water or an alcohol to give the amide.

By the "cleavage" of an amide bond is meant the hydrolysis of an amide group to give a carboxy-containing molecule and a primary or secondary amino compound.

By the "formation" of an ester bond is meant the condensation of a carboxyl-containing molecule with a primary or secondary alcohol with elimination of water to give the ester.

By the "cleavage" of an ester bond is meant the hydrolysis of an ester group to give a carboxyl-containing molecule and a primary or secondary alcohol.

By the term "mutant" or "mutated" or "modified " subtilisin enzyme(s) is meant to include a subtilisin enzyme, or a homologous serine protease, in which at least one amino acid has been changed so that the mutant enzyme has an enhanced thermostability when compared to that for the wild-type enzyme. The mutated or modified subtilisin enzymes are also described herein as "subtilisin material."

As used herein, and under the definition of mutant or mutated or modified subtilisin enzyme or subtilisin material, "homologous" means that a serine protease has at least 50%, and preferably 80% amino acid sequence homology with the sequences reference above for subtilisin BN', subtilisin Carlsberg, subtilisin DY, subtilisin amylosachariticus, mesenticopeptidase, thermitase, proteinase K, or thermomycolase. For example, ESPERASE[R] (Novo), MAXACAL[R] (Gist Brocade), SAVINASE[tm] (Novo) and Proteinase K are subtilisins within the scope of the term "homologous."

By "enhanced thermostability" is meant resistance to thermal inactivation; that is, the ability of a mutant enzyme to retain a specific catalytic activity at a given temperature longer than the wild type enzyme. In a preferred embodiment, resistance to thermal inactivation is measured under two representative sets of conditions. The first is in the presence of 10 mM calcium chloride at 65° C. and the second is in the presence of 10 mM EDTA at 45° C., which removes free calcium from solution. Calcium is known to stabilize subtilisin. Measurements of stability of the protease activity of the mutant subtilisins are also made under these two extremes of calcium concentration. The halflife ($T_{\frac{1}{2}}$) of wild type BPN' subtilisin is 59±3 minutes in 10 mM CaCl at 65° C. and 14.4 ±0.05 minutes in 1 mM EDTA at 45° C. The thermostability of the protease activity of the mutant subtilisin is expressed as a ratio of $T_{\frac{1}{2}}$ (mutant) divided by the $T_{\frac{1}{2}}$ (wild type). A mutant subtilisin is said to be thermostable when that ratio, under either set of conditions outlined above, is greater than 1.0.

DETAILED DESCRIPTION OF THE INVENTION

This invention pertains to novel uses of subtilisin enzymes that have been modified by mutating the amino acid sequence of the enzymes. The mutated subtilisin enzymes of this invention were designed to have enhanced thermostability. Surprisingly it has been found that they are of unexpected utility as catalysts in organic syntheses under conditions wherein wild type or non-mutated subtilisin would be much less active and/or catalytically stable.

The subtilisin enzymes of this invention belong to a class of enzymes known as proteases. A protease is a catalyst which cleaves peptide bonds. An example of this cleavage is given below.

A dipeptide containing two amino acids joined through a peptide bond

Two amino acids

The specific catalytic activity of a protease which is responsible for cleavage of a peptide bond is an amidase activity. To catalyze the reverse reaction, synthesis of a peptide bond, the protease must also contain a catalytic activity known as an esterase activity. Proteases containing an esterase activity can function as a peptide ligase, that is they can be used to join peptides by creating a peptide bond between the individual peptides or amino acids in the presence of an amino acid acyl donor and an amino acid acyl acceptor. The two activities are distinct and it is possible to destroy the amidase activity while retaining a protease's esterase activity. Thiolsubtilisin is an example of such a protease which retains only the esterase function.

The individual amino acid mutations detailed in Table 1 are examples of mutations that have been found to be thermostabilizing mutations. Thus, the mutated subtilisin enzymes of this invention have at least one amino acid position substitution that also enhances thermostability. In Table 1, the naturally occurring amino acid and position number is given first with the arrow to the right indicating the amino acid substitution. The mutations were made using subtilisin BPN'. However, as explained herein, these mutations can be introduced at functionally analogous positions in other serine proteases using oligonucleotide-directed mutagenesis.

TABLE 1

Mutations in subtilisin BPN'

1. Val8→Ile
2. Thr22→Cys, Ser87→Cys
3. Thr22→Lys, Asn76→Asp
4. Met50→Phe
5. Ser53→Thr
6. Ser63→Asp, Tyr217→Lys
7. Asn76→Asp
8. Ser78→Asp
9. Tyr104→Val, Gly128→Ser
10. Ala116→Glu
11. Leu126→Ile
12. Gly131→Asp
13. Gly166→Ser
14. Gly169→Ala
15. Pro172→Asp
16. Pro172→Glu
17. Ser188→Pro
18. Gln206→Cys
19. Gln206→Tyr
20. Ala216→Cys, Gln206→Cys
21. Tyr217→Lys
22. Tyr217→Leu
23. Asn218→Asp
24. Gln206→Tyr
25. Ser248→Asp, Ser249→Arg
26. Thr254→Ala
27. Gln271→Glu

Table 2 shows the strain designation of the host cells into which the mutant subtilisins have been cloned and compares the half-life of each mutant enzyme to that of the wild type enzyme. The results are expressed as the result as the ratio of the half-life of the mutant enzyme to that of the wild type enzyme.

TABLE 2

Mutated Subtilisin BPN' Enzymes.

| Strain | Mutation | T½ compared to wild type enzyme 10 mM CaCl | 1.0 mM EDTA |
|---|---|---|---|
| GX7130 | Wild Type | 1.0 | 1.0 |
| GX7174 | VAL8→ILE | 2.0 | 0.8 |
| GX7175 | GLY169→ALA | 5.9 | 1.1 |
| GX7181 | ASN218→ASP | 5.2 | 4.0 |
| GX7186 | THR22→CYS SER87→CYS ASN218→SER | 29 | 5.3 |
| GX7195 | TYR217→LYS | 3.3 | 2.7 |
| GX7199 | THR22→CYS SER87→CYS GLY169→ALA PRO172→ASP | 10 | |
| GX8303 | MET50→PHE | 0.76 | 1.4 |
| GX8309 | SER248→ASP SER249→ARG | 1.5 | 0.75 |
| GX8314 | GLN206→CYS | 2.4 | 5.1 |
| GX8321 | THR22→CYS SER87→CYS GLY169→ALA MET50→PHE TYR217→LYS ASN218→SER | — | 36 |
| GX8324 | THR22→CYS SER87→CYS GLY169→ALA MET50→PHE TYR217→LYS ASN218→SER GLN206→CYS | — | 168 |
| GX8330 | TYR217→LEU | 2.0 | 1.8 |
| GX8336 | GLN206→TYR | 1.1 | 1.7 |
| GX8350 | MET50→PHE GLY169→ALA GLN206→CYS TYR217→LYS ASN218→SER ASN76→ASP | | 400 |
| GX8352 | SER63→ASP TYR217→LYS | 6.3 | — |
| GX8354 | GLN271→GLU | 1.3 | — |
| GX8363 | THR22→LYS ASN76→ASP | 1.3 | 2.1 |
| GX8372 | MET50→PHE GLY169→ALA GLN206→CYS TYR217→LYS ASN76→ASP SER78→ASP ASN218→SER | — | 630 |
| GX8376 | TYR104→VAL GLY128→SER | 5.0 | 1.6 |
| GX7148 | GLY131→ASP | 1.5 | 0.9 |
| GX7150 | ASN218→SER | 3.5 | 2.6 |
| GX7164 | ASN218→ASP | 1.9 | 1.5 |
| GX7178 | SER188→PRO | 1.8 | — |
| GX7188 | ALA116→GLU | 1.3 | 1.05 |
| GX7189 | LEU126→ILE | 1.4 | 1.1 |
| GX8301 | ASN218→SER GLY166→SER | 7.4 | — |
| GX8305 | SER53→THR | 2.0 | — |
| GX8306 | ASN218→SER THR254→ALA | 7.0 | — |
| GX8315 | ASN218→SER GLY131→ASP THR254→ALA | 11.4 | — |
| GX7159 | THR22→CYS SER87→CYS | 1.05 | 1.5 |
| GX8307 | GLN206→CYS SER87→CYS GLN206→CYS GLN206→CYS ALA216→CYS | | |
| GX7172 | PRO172→ASP | 1.5 | 1.1 |
| GX8312 | PRO172→GLU | 2.0 | 1.0 |
| GX8347 | ASN76→ASP | — | 2.5 |
| GX8364 | SER78→ASP | — | 1.5 |
| GX8373 | ASN218→ASP MET50→PHE GLY169→ALA GLN206→CYS TYR217→LYS ASN76→ASP SER78→ASP | — | 400 |

Using the information of the subtilisin enzyme mutations of Tables 1 and 2, one can use site directed mutagenesis techniques to easily modify other proteases which are closely related so that they contain functionally equivalent improvements. For example, one might modify subtilisin Carlsberg. Closeness of relation of proteases is measured by comparison of amino acid sequences. There are many methods of aligning protein sequences, but the differences are only manifest when the degree of relatedness is quite small. The methods described in *Atlas of Protein Sequence and Structure*, Margaret O. Dayhoff editor, Vol. 5 Supplement 2, 1976, National Biomedical Research Foundation, Georgetown University Medical Center, Washington, D.C., p. 3 ff., entitled SEARCH and ALIGN, define relatedness. As is well known in the art, related proteins can differ in number of amino acids as well as identity of each amino acid along the chain. That is, there can be deletions or insertions when two structures are aligned for maximum identity. Alignment for maximum identity allows one to identify corresponding amino acid positions in two subtilisins which are the functional equivalent of each other. For example, subtilisin Carlsberg has only 274 amin acids, while subtilisin BPN' has 275 amino acids. Aligning the two sequences shows that Carlsberg has no residue corresponding to ASN56 subtilisin BPN'. If only the position number itself were considered, the amino acid sequence of subtilisin Carlsberg would appear very different from BPN'. However, by recording a gap at location 56, it is clearly apparent that the sequences are highly homologous. Therefore, one can predict with high degree of confidence that, for example, if substituting SER for ASN at location 218 of subtilisin BPN' will increase thermostability, then substituting SER for ASN at location 217 of subtilisin Carlsberg will also increase thermostability as position 217 of subtilisin Carlsberg is the functionally analogous position of amino acid at position 218 of subtilisin BPN'.

One can use this reasoning to apply all of the thermostable mutations described herein to other homologous serine proteases. Further, other mutations resulting in thermostability are encompassed by this invention as well.

Mutant subtilisin enzymes useful in the methods of the invention can be constructed by recombinant DNA techniques or by chemical techniques, especially chemical techniques utilizing the methods of the invention. For example, to produce a mutant subtilisin enzyme useful in the methods of the invention by recombinant DNA techniques, the gene coding for the desired subtilisin material generally is first isolated from its natural source and cloned in a cloning vector. Alternatively, mRNA which is transcribed from the gene of interest can be isolated from the source cell and converted into cDNA by reverse transcription for insertion into a cloning vector. A cloning vector can be a phage or plasmid, and generally includes a replicon for autonomous replication of the vector in a microorganism independent of the genome of the microorganism. A cloning vector advantageously includes one or more phenotypic markers, such as DNA coding for antibiotic resistance, to aid in selection of microorganisms transformed by the vector.

Procedures for insertion of DNA or cDNA into a vector for cloning purposes are well known in the art. These procedures generally include insertion of the gene coding for the subtilisin material into an opened restriction endonuclease site in the vector, and may involve addition of homopolymeric tails of deoxynucleotides to the ends of the gene and linking the gene to opened ends of a cloning vector having complementary homopolymeric tails. A subtilisin gene can then be mutated by oligonucleotide-directed mutagenesis. Oligonucleotide-directed mutagenesis, also called site-directed mutagenesis, is described in detail in Bryan et al., *Proc. Natl. Acad. Sci. USA* 83:3743-3745 (1986), incorporated herein by reference.

The mutant subtilisins are useful in any organic synthesis reaction which involves either the formation or cleavage or an amide or ester bond. In a preferred embodiment, the organic synthesis reaction is an acylation reaction. In another preferred embodiment, the organic synthesis reaction results in the formation of a peptide bond, and is used in peptide or protein synthesis.

The enzymatic reactions catalyzed by the mutant subtilisins of the invention are highly stereoselective, racemization-free, and require a minimal of side-chain protection in the coupling steps.

Also, because of their unusual stability in aqueous and organic cosolvents, the mutant subtilisin enzymes of the invention offer distinct advantages over the use of other proteases in the methods of the invention. The mutant subtilisins function as active catalysts in organic solvents of high concentration. Also, anhydrous media can be used to carry out reactions sensitive to water.

Therefore, in one preferred embodiment the methods of the invention utilize mutant subtilisins as enzymatic catalysts in a reaction medium comprising an anhydrous organic solvent. In another preferred embodiment, the methods of the invention utilize mutant subtilisins as enzymatic catalysts in a reaction medium comprising at least 10% of a water-miscible organic solvent.

To be useful in the methods of the invention, the anhydrous organic solvent must have sufficient ionizing power to both dissolve the ionic reagents in the reaction and to promote the dissociation of organic molecules. The ionizing power of a solvent depends on its dielectric constant, that is, its ability to insulate charges from each other, and on its ability to solvate ions by formation of ion-dipole bonds. Examples of suitable anhydrous media include DMF, formamide, dimethyl sulfoxide (DMSO), sulfolane, tert-amyl alcohol, tetrahydrofuran, acetone, dichloromethane, pyridine, toluene, acetonitrile, ethyl acetate, 1,4-butanediol, dioxane and DHF.

The advantage of performing the reaction in the presence of at least 10% of a water-miscible organic solvent is that some reactants, such as protected peptides, are much more soluble in organic solvents than they are in a purely aqueous medium. By "water-miscible organic solvent" is meant those organic liquids which are miscible with water in any proportion to form a single phase system. Examples of suitable organic solvents include alcohols, polyols, nitriles, and ethers, for example, methanol, ethanol, propanol, isopropnaol, butanol, isobutanol, sec-butanol, tert-butanol, amyl alcohol, iso-amyl alcohol, hexanol, 2-ethylbutanol, octanol, iso-octanol, mirystyl alcohol, palmytyl alcohol, stearyl alcohol, vinyl alcohol, allyl alcohol, butenyl alcohol, propargyl alcohol, oleyl alcohol, cyclobutanol, cyclopentanol, cyclohexanol, phenol, o-, m- and p-cresol, isopropylphenol, t-butylphenol, benzyl alcohol, ethylene glycol, propylene glycol, butylene glycol, hexylene glycol, 1,6-hexyne diol, diethylene glycol, low molecular weight polyethylene glycol and polypropropylene glycol, 1,4-butanediol, diethylene glycol, acetonitrile, dioxane, tetrahydrofuran, DMF and the other solvents listed above for use in anhydrous media.

The sugar moiety of carbohydrates and other sugar-containing compounds such as nucleosides may be regioselectively acylated or esterified using mutant subtilisins and the methods of the invention. For example, the mutant subtilisins described above may be used in the methods of the invention to selectively acylate sugar resides of nucleosides by a transesterification reaction. The mutant subtilisins contain the active center nucleophile mechanistically essential for transesterification. Transesterification may be described by the reaction:

RCOOR' + sugar → RCOO-sugar monoester + R'OH where R is an aliphatic moiety. Transesterification using the mutant subtilisins require an organic solvent as the reaction medium because in aqueous solutions water will replace sugar as a nucleophile, thus leading to hydrolysis instead of transesterification. Appropriate solvents for the transesterification of sugars are very hydrophilic organic solvents in which the sugar is soluble and the mutant subtilisin is active, such as anhydrous, dry DMF.

Preferably the alcohol product of the transesterification, R'OH, is removed or is unstable and converts to another chemical form such as a ketone or aldehyde. This prevents the reverse reaction from occurring and increases the yield of the RCOO-sugar monoester product. One example of how to drive the reaction in this manner is to use an enol ester as the acyl group donar in the transesterification reaction. Cleavage of the enol ester produces an unstable alcohol which naturally rearranges to a stable ketone or aldehyde form (Wong, Y. F. et al., *J. Am. Chem. Soc.* 110:7200 (1988), and Wong, Y. F. et al., *J. Org. Chem.* 53:3127 (1988)). For example, when isopropenyl acetate is used as the donar of the acetate group in the transesterification of the sugar residues of nucleosides as described above, the stable products are the 5'-0-acetyl-sugar and acetone. esterification of the 5'-hydroxyl group of deoxynucleosides with the acetyl group, using the mutant subtilisins and methods of the invention, in fewer steps than previously possible provides increased yields of the 5'-acetyl deoxynucleosides, precursors useful in dideoxynucleoside synthesis.

Examples of sugars which may be selectively acylated by the methods of the invention include sugars of any chain length such as those containing three carbons (trioses), four carbons, five carbons (pentoses), six carbons (hexoses), seven carbons (heptoses) and the like, for example, ribose, deoxyribose, ribulose, glucose, fructose, mannose, galactose, sedoheptulose, erythrose, xylulose and arabinose; sugar-containing oligomers which contain a sugar conjugated to other sugars to form a disaccharide or larger oligomer such as sucrose, glycogen, cellobiose, lactose, maltotriose and maltose; and sugar-containing compounds which contain a sugar or sugar oligomer conjugated to a non-sugar species or aglycon such as to a purine, pyrimidine, amino acid, lipid or other organic compound, for example, nucleosides, riboflavin, and salicin.

Examples of nucleosides which may be selectively acylated by the methods of the invention include those containing a purine or pyrimidine base which is condensed with a pentose or a deoxypentose sugar, such as deoxyadenosine, adenosine, deoxyinosine, inosine, deoxycytidine, cytidine, 2'azido-2'-deoxycytidine, thymidine, 3'-azido-3'-dioxythymidine (AZT), deoxyguanosine, guanosine, uridine, 2'azido-2'-deoxyuridine, pseudouridine and the like.

The function of the mutant subtilisins in the peptide bond reaction is the catalytic acceleration of the attainment of the equilibrium for formation of the peptide bond. The effectiveness of the protease is greater the more specific the protease is for the substrates. The pH optimum of the peptide bond synthesis lies in the pH range between the pK of the α-carboxyl group and that of the amino group of the substrates, and is normally between pH 6 and pH 7. Depending on the concentration and the catalytic activity of the protease as well the affinity of the protease for the substrates, the time necessary to complete the reaction may be several minutes or several days.

Thermodynamically controlled peptide synthesis, that is, the direct reversal of the catalytic cleavage of peptides using the mutant subtilisins of the invention, can be employed in conjunction with amino acids which have carboxy components protected or unprotected at the C-terminus. Generally, the N-acetylated amino acid (or peptide) ester will act as an acyl donor and an amino acid amide will act as the acceptor amine. Because of the specificity of the mutant subtilisins for the acyl donor and acceptors, it is not usually necessary to protect (block) the side chains on the amino acid reactants.

Suitable removable groups with which to derivatize peptides or amino acids at their N-terminus to facilitate their use in peptide synthesis include the p-chlorophenyl group; the formyl group; the acetyl group; the N-carbobenzoxy (CBZ) group tertiary alkoxycarbonyl groups such as t-butyloxylcarbonyl (BOC-), t-amyloxycarbonyl (t-Aoc); benzyloxycarbonyl groups which can be substituted with an inert substituent such as benzyloxycarbonyl (Z-), p-methoxybenzyloxycarbonyl (PMZ-), 3,5-dimethoxybenzyloxycarbonyl (Z(OMe)$_2$-), 2,4,6-trimethylbenzyloxycarbonyl (TMZ-), p-phenylazobenzyloxycarbonyl (PZ-), p-toluenesulfonyl (tosyl-); o-nitrophenyl sulfenyl (Nps-) and the like.

The hydrolysis of esters and amides catalyzed by the mutant subtilisins of the invention is similar in mechanism but different in rate-determining steps. In amide cleavage (or hydrolysis), formation of acyl-intermediates is rate-determining and pH independent at pH's higher than the pK of the active site His-imidazole; in ester cleavage (or hydrolysis) deacylation is rate-determining, general-base catalyzed, and pH dependent. Ester cleavage may also be performed in an aqueous medium. Therefore, without undue experimentation, one of ordinary skill in the art will be able to devise conditions wherein specific enzymatic activities, such as the amidase or the esterase activity, predominate.

Water-miscible organic solvents increase the pK value of the α-carboxyl group of the carboxy component and thus decrease the acidity of that group and decrease the concentration of the uncharged, reactive substrate. Water-miscible organic solvents only marginally influence the pK value of the amino group of the nucleophile. For example, the pK value of acetyl glycine in water is 3.60, while in 80% (v/v) dimethylsulfoxide it is 6.93; the pK values of Gly-NH$_2$, 8.20 and 8.10, respectively, remains almost constant.

Suitable amino acids which can be joined in the formation of a peptide bond include alanine, serine, aspartic acid, arginine, valine, threonine, glutamic acid, leucine, isoleucine, proline, glycine, cysteine, tyrosine, tryptophan, histidine, asparagine, phenylalanine, lysine, methionine, glutamine and hydroxyproline and their derivatized forms. Either the D- or the L-amino acid may be used.

The amidase activity of the subtilisin mutant can also be suppressed by addition of an appropriate amount of a water-miscible organic solvent. In general, a solution containing more than 50% of an organic solvent such as DMF, dioxane or DMSO is required to selectively remove the amidase activity. This enables the use of the esterase activity of the mutant subtilisin enzymes to polymerize amino acid esters and to join peptide fragments via aminolysis with mutants and under conditions where the amidase activity would not otherwise by suppressed.

The methods of the invention are useful for the resolution of chiral alcohols and acids through the formation or hydrolysis of an ester bond.

The methods of the invention may also be performed when the mutant subtilisins serve as catalysts while immobilized on a solid phase support, for example, tresyl chloride-activated agarose.

The thermostable subtilisin mutants may be further modified by chemically-derivatizing specific amino acids. For example, the amidase activity of the mutant subtilisins of the invention may be selectively damaged by creating the mutant thiolsubtilisin derivative of the mutant subtilisin. In a similar manner, modification of the active site histidine residue would allow the mutant enzyme to be used as an entropic trap in the methods of the invention to synthesize peptides because the primary binding properties of the enzyme are retained.

The methods of the invention have application in the synthesis of acylated deoxynucleoside precursors which can be readily converted to the dideoxynucleosides, especially dideoxyadenosine, dideoxycytidine and dideoxyinosine, and in the synthesis of biologically active peptides, antibiotics, synthetic vaccines, hormones, sugars, and the like.

Having now described the invention in general terms, the same will be further described by reference to certain specific examples that are provided herein for purposes of explanation only and are not intended to be limiting unless otherwise specified.

EXAMPLES

EXAMPLE 1

Construction of Subtilisin 8350

Six mutations of subtilisin BPN' which stabilized the protease activity of the enzyme against thermal inactivation were combined to create the highly thermostable subtilisin 8350; these mutations changed position 50 from Met to Phe, position 169 from Gly to Ala, position 76 from Asn to Asp, position 206 from Gln to Cys (Cys-SH), position 217 from Tyr to Lys and position 218 from Asn to Ser. The changes at positions 50 and 160 affected the peptide's hydrophobic interactions, position 76 the electrostatic interaction, position 206 the van der Walls interaction and positions 217 and 218 H-bonding. Three stabilizing mutations were discovered in an anti-parallel beta-loop region (residues 202-219 of the enzyme). These were Asn 218 to Ser, Tyr 217 to Lys, and Gln 206 to Cys which is spontaneously oxidized to cysteine persulfide. The Asn 218 to Ser mutant has been described in detail (Bryan, P.N. et al., *Proteins: Structure, and Genetics* 1:326 (1986)). The related thermophilip proteases thermitase, thermomycolase, and proteinase K also contain this Ser 218 mutation (Bryan, P.N. et al., *Proteins: Structure, and Genetics* 1:326 (1986)). The mutation Tyr 217 to Lys also results in improved enzyme thermostability. The cysteine perfulfide at position 206 results in a significantly more thermostable enzyme probably through enhancement of van der Waal interactions. Reduction of the persulfide group leaves an enzyme which is less thermostable than the native protein. Cysteine persulfide is known to be formed under fermantation conditions (Morra, M.J. et al., *Soil Sci. Soc. Am. J.* 49:882-6 (1985)) and has been identified as a component of certain naturally occurring proteins (Ploegman, J.G. et al., *J. Mol. Biol.* 127:149-162 (1979)). Two other thermostabilizing mutations - Gly 169 to Ala, Met 50 to Phe - improve the hydrophobic packing of the folded enzyme.

The final mutation was designed to enhance the thermostability by incorporating the isosteric replacement of Asn 76 with Asp thus increasing the electrostatic interaction at a calcium binding site (Pantoliano et al., *Biochemistry* 27:8311 (1988)).

An X-ray crystal structure has been determined for the engineered subtilisin 8350. Conformation changes were found to be subtle and highly localized, the additive increases in the free energy of stabilization and the approximately multiplicative increases in the half-time of thermal inactivation (Bryan, P.N., *Biotechnology Advances* 5:221 (1987)), which result from combining several independent thermostabilizing mutations, has provided a highly thermostable enzyme.

EXAMPLE 2

Thermostability of Subtilisin 8350 in Non-Native Environments

Figure 1:
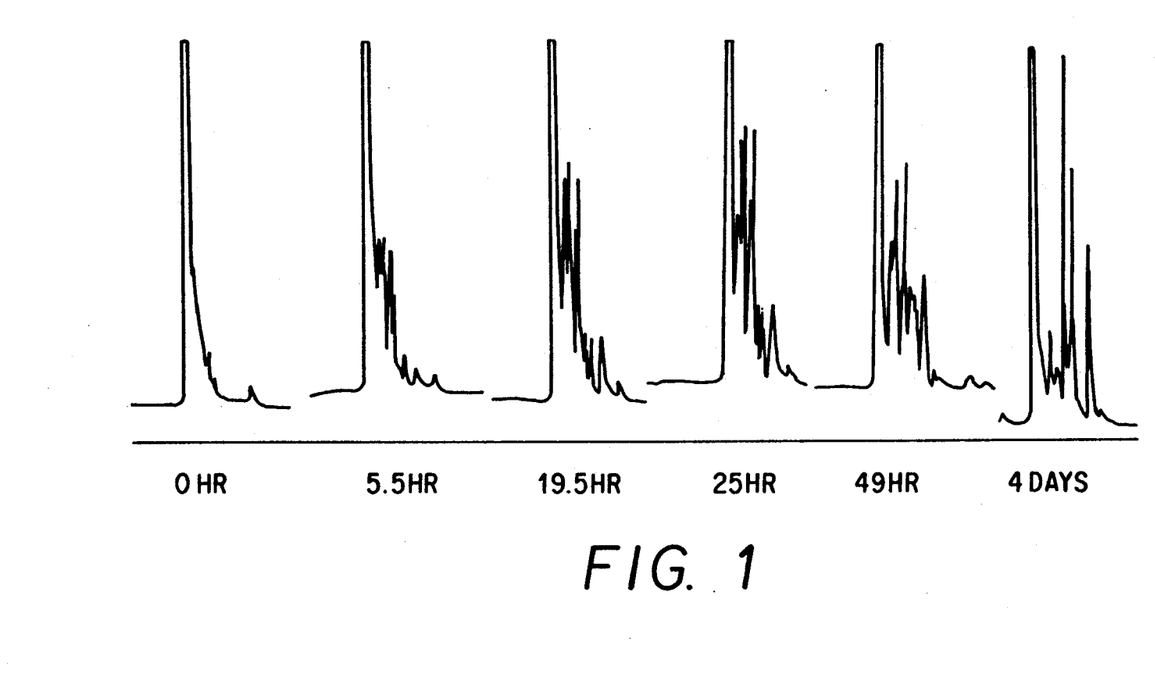
FIG. 1 is a Fast Protein Liquid Chromatography (FPLC) trace obtained by monitoring the autolysis of the wild type subtilisin BPN on a Sepharose 12 GPC column using 50 mM sodium formate, pH 4.8, as the eluent.
Figure 2:
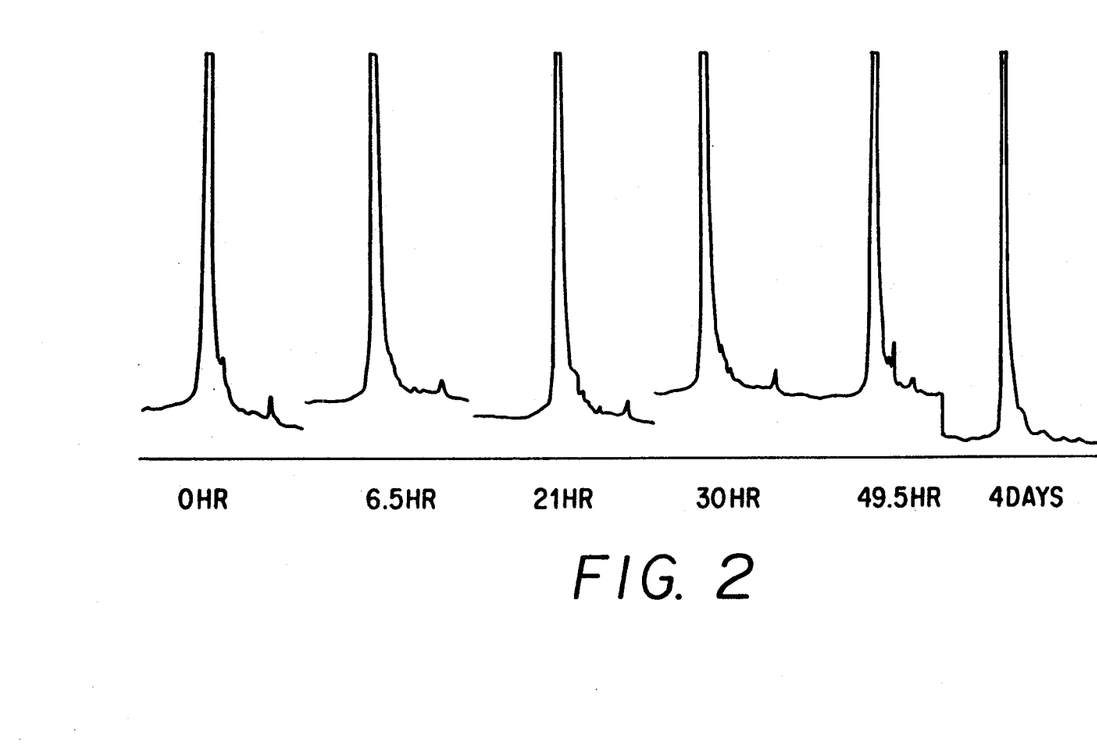
FIG. 2 is a FPLC trace obtained from monitoring the stability of subtilisin 8350 on a Sepharose 12 GPC column using 50 mM sodium formate, pH 4.8, as the eluent.
Figure 3:
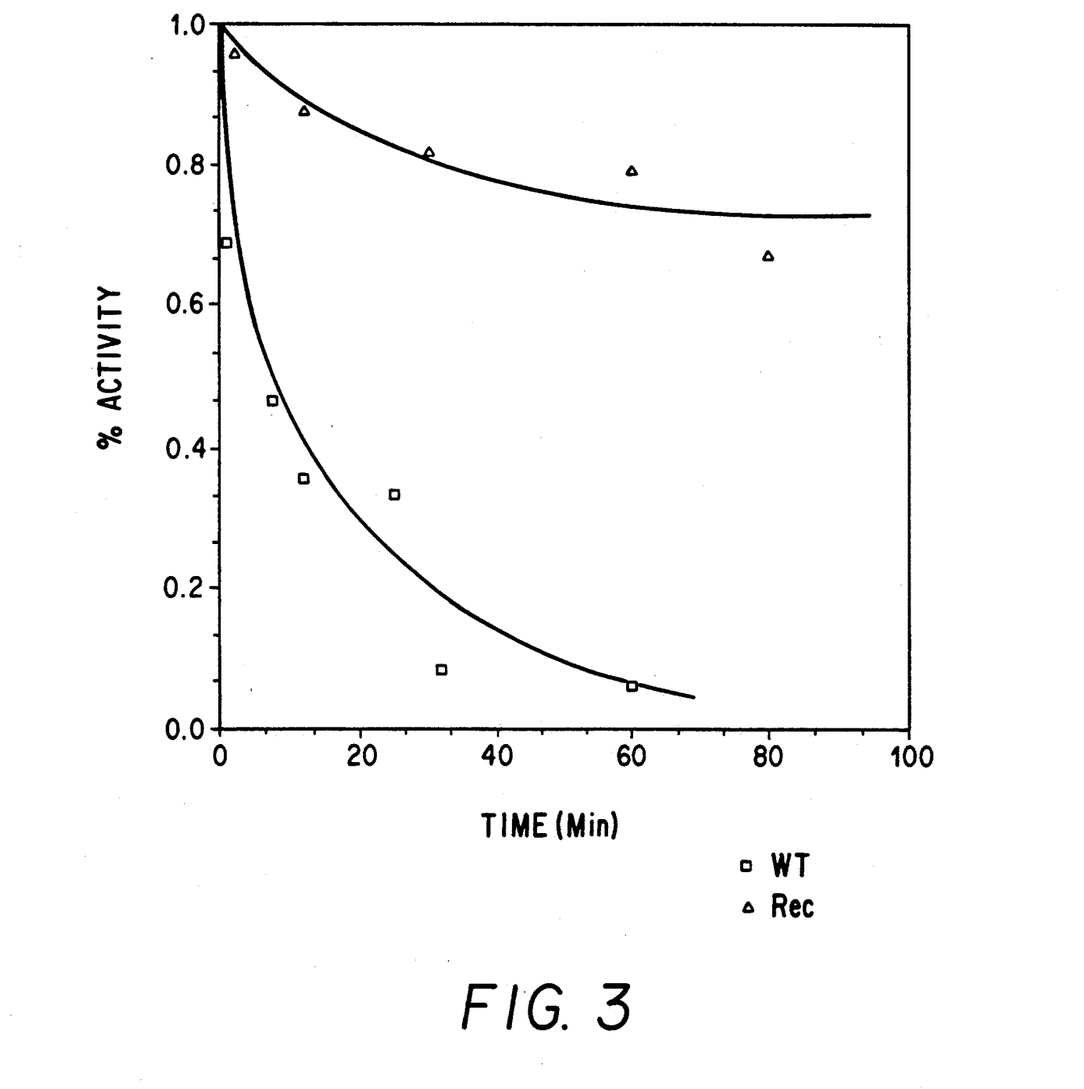
FIG. 3 shows the stability of wild type subtilisin BPN (wild type) and recombinant subtilisin 8350 (recombinant) in anhydrous dimethylformamide (DMF).

The thermostability of the proteolytic activity of recombinant subtilisin 8350 enzyme was compared to that of the wild type protein and was evaluated by assaying the autodegradation of the enzyme (FIGS. 1-3).

Unfolding of the native enzyme leading to autolysis results in a gradual loss of proteolytic activity in aqueous solution (Takahashi, K. et al., *Biochemistry* 20:6185-90 (1981)). The rapid autolytic degradation of the native enzyme in an aqueous solution was confirmed by Fast Protein Liquid Chromatography (FPLC) as shown in FIG. 1.

FIG. 2 shows a series of FPLC traces which show that the mutant enzyme is highly stable toward autolysis. The increased stabilization of the folded state in the mutant enzyme decreases transient unfolding of the protein and thereby inhibits autolysis.

Although a gradual loss of wild type subtilisin protease activity was observed in aqueous solution, a precipitous drop in activity was observed in anhydrous DMF (FIG. 3). Most proteins are rapidly denatured by the strong solvent anhydrous DMF (Lapanje, S., *Physicochemical Aspects of Protein Denaturation*, Wiley, New York, chapter 3.7 (1978)). This is most likely cause of its precipitous drop in activity observed for the wild type enzyme under these conditions. FIG. 3 also shows the stability of the proteolytic activity of recombinant subtilisin 8350 in anhydrous DMF. Again the cumulative stabilizing effects of the multiple mutations appear to have inhibited denaturation of the mutant enzyme. This allows the mutant subtilisin to retain its active conformation in the harsh environment of anhydrous DMF.

EXAMPLE 3

Use of Subtilisin 8350 in the Regioselective Acylation of Sugars

THF and pyridine had been used extensively in the regioselective acylation of sugars by lipases (Therisod, M. et al., *J. Am. Chem. Soc.* 109:3977-3981 (1987); Therisod, M. et al., *J. Am. Chem. Soc.* 108:5638-5640 (1986)). Lipases are a different class of enzyme than are proteases and they do not contain natural proteolytic activity. Although the subtilisin 8350 was found to be largely inactive in both THF and pyridine it was found to be highly active as an regioselective acylation catalyst in anhydrous, dry DMF. Previous use of lipases in the acetylation of furanosides gave good yields and high regioselectivity for the ribo-, xylo-, and arabinofuranosides; poor regioselectivity, however, was observed for methyl 2-deoxyribofuranoside. Addition of the subtilisin 8350 mutant in anhydrous, dry DMF using isopropenyl acetate as the acetyl donor gave a 70% yield of methyl 5-0-acetyl-D-ribofuranoside in 24 h. The unreacted starting material was the only other observed reaction component.

EXAMPLE 4

Use of Subtilisin 8350 in a Non-Native Environment for Enzymatic Acylation of Nucleosides The following general procedure was used in performing the regioselective acylations of the nucleosides listed in Table 3.

One mmol of nucleoside was dissolved in 2-4 mL of dry DMF and warmed. The solution was cooled to 45° C. and 1.1 mL (10 eq) of isopropenyl acetate and 260 mg of pulverized subtilisin 8350 powder were added. The suspension was shaken at 45° C. After 24 h an additional 130 mg of enzyme was added to the reaction mixture. After the appropriate times, as indicated in Table 3, the reaction mixture was filtered and the filtrate was evaporated to dryness. The residue was purified by silica gel chromatography using mixtures of ethyl acetate:methanol:water as the eluent for the times indicated. The isolated products were obtained in the yields shown in Table 3.

The positions of acetylation were determined by NMR spectroscopy and by comparison with reported values according to published literature references for the non-enzymatic syntheses of these compounds (see below). $^1$H and $^{13}$C NMR were obtained at 200 MHz and 50 MHz respectively on a Varian XL-200 spectrometer. Mass spectra were obtained on a Hewlett-Packard 5995C quadrapole gas chromatographmass spectrometer operating at 70 eV. Thin-layer chromatography was done on 0.25-mm layers of silica gel (60 A) which contained a fluorescent indicator. Column chromatography was done using Baker flash chromatography silica gel (230-400 mesh). Fasts Protein Liquid Chromatography (FPLC) was done on a Pharmacia system comprised of two P-500 pumps, a GP-250 gradient programmer, and a single path UV-1 monitor using a Sepharose 12 GPC column. The FPLC column eluent was 50 mM sodium formate pH 4.8 at a flow rate of 0.5 mL/min.

The enzymatic acetylation of thymidine was accomplished in DMF at 45° C. using commercially available isopropenyl acetate as the acyl donor and subtilisin 8350 as the catalyst for 36 h. A quantitative yield of 5'-0-acetylthymidine was obtained. Thus enzymatic acetylation followed by deoxygenation (Hitsuya, H. et al., *Proc. Nat'l. Acad. Sci. USA* 83:1911 (1986)) allows the overall yield of 3'-deoxythymidine from thymidine to be doubled while at the same time employing fewer steps. Similar enhancements of yields were observed (see Table 3) for the enzymatic preparation of 5'-acetyl derivatives of 2'-deoxycytidine and 2'-deoxyadenosine over the previously reported (Ihido, Y. et al., *J. Chem. Soc.* 2088 Perkin Trans. 1 (1979)) two-step procedures.

Three steps are usually required to prepare the 5-0-acylribonucleosides (Brown, D. M. et al., *J. Chem. Soc.* 3299 (1950); Mitzuna, Y. et al., *J. Org. Chem.* 40:1385 (1975)). Two-step procedures involving selective deacetylatino of the di- or triacetates have also been reported (Ihido, Y. et al., *J. Chem. Soc.* 2088 Perkin Trans. 1 (1979); Griffin, B. E. et al., *Proc. Nat'l Acad. Sci. USA* 51:440-444 (1964); Brown, D. M. et al., *J. Chem. Soc.* 2388 (1956)) but the overall yields are often low. Subtilisin 8350 efficiently catalyzed the regioselective acetylation of ribonucleosides in DMF (see Table 3). Small portions (<5%) of diacetylated byproducts were observed to form when additional enzyme (>2 weight equivalents) and extended reaction times (48 h) were used to obtain higher yields of the desired 5'-0-acetyl derivatives. The formation of diacetyl byproducts may be attributed to the stereoelectronic effects which have been observed in the differential reactivities of the hydroxyl groups, and hence the product distributions, obtained during acylation (Kamaike, K. et al., *Nucleic Acids Res. Symposium* Series No. 16, IRL Press, Oxford, pp. 177-180 (1985)) and deacylations (Griffin, B. E. et al., *Proc. Nat'l Acad. Sci. USA* 51:440-444 (1964)) of nucleosides.

TABLE 3

Regioselective acetylation of nucleosides and sugars with Subtilisin 8350.

| Cpd | R | Substrate B | Name | Time (days) | Yield (%) |
|---|---|---|---|---|---|
| 1 | H | (thymine) | Thymidine | 1.5 | 100 |
| 2 | OH | (uracil) | Uridine | 1 | 80 |
|   |    |            |         | 2 | 90 |
| 3 | H | (cytosine) | 2-Deoxycytidine | 1 | 60 |
|   |   |            |                 | 2 | 80 |
| 4 | OH | (cytosine) | Cytidine | 1 | 60 |
|   |    |            |          | 2 | 80 |
| 5 | H | (adenine) | 2-Deoxyadenosine | 1 | 50 |
|   |   |           |                  | 2 | 80 |
| 6 | OH | (adenine) | Adenosine | 1 | 40 |
|   |    |           |           | 2 | 65 |
| 7 | H | CH$_3$O | Methyl 2-deoxy-D-ribofuranoside | 1 | 70 |

EXAMPLE 5

Comparison of Chemical Peptide Synthesis with Enzymatic Peptide synthesis Using the Subtilisin 8350 Mutant a) Chemical synthesis of Peptides

All authentic peptides were synthesized by the mixed anhydride method (Anderson, G. M. et al., *J. Am. Chem. Soc.* 89:5012 (1987)). In a typical synthesis, 470 mg (1.5 mmole) of Z-L-Tyr-OH and 150 mg of N-methylmorpholine were dissolved in dry THF (10 mL), and the solution was cooled to $-15°$ C. in a carbon tetrachloride/dry ice bath. To this mixture was added 204 mg of isobutyl chloroformate and the solution was stirred for 1 min. A solution of 390 mg (1.5 mmole) of L-arg-OME2HCl and 0.21 mL of N-methylmorpholine in 3 mL of dry DMF was added and the solution stirred for 5 min. The reaction was allowed to come to room temperature, the hydrochloride salt was filtered off, and the solution was concentrated under vacuum. The residue was dissolved in 1-butanol (or ethyl acetate, for peptides not containing arginine), and washed with water, 1 N HCl, water, 0.2 M NaHCO$_3$, and water. The organic phase was separated, dried with MgSO$_4$, and concentrated under vacuum. The resulting oil was rubbed with ethyl ether to give a solid, which was recrystallized from EtOH/hexanes; yield 0.42 g (56%).

Enzyme Assays

Enzyme activity was assayed photometrically by measuring the absorbance increase at 405 nm due to release of p-nitrophenol ($\epsilon = 18.5$ mM$^{-1}$cm$^{-1}$) from Z-L-Tyr-p-nitrophenyl ester (Z-L-Tyr-ONp). The assay buffer contained 0.2 M tris-maleate (pH 6.8), 0.1 M CaCl$_2$, and 10% dioxane. Substrate solution was 2.4 mM Z-L-Tyr-ONp in dioxane. Typical assay contained 2.8 mL of buffer, 0.1 mL substrate solution, and 0.02 mL of enzyme solution being assayed.

HPLC Analysis

All yields were determined by HPLC on a Gilson Model 43 chromatograph equipped with a Data Master gradient programmer/data manipulation package. The chromatograph was equipped with a Vydac C-18 column (25×0.46 cm) and a variable wavelength UV detector. Flow rate in all experiments was 1.0 mL/min. Peaks were detected at 280 nm for tyrosine-containing peptides and at 254 nm for others. Peak identification was made by coelution with compounds authenticated by NMR and/or amino acid analysis. Peak intensities were used to calculate relative concentrations. With a given buffer preparation, retention times varied by no more than 3%. Aliquots of enzymatic reactions (20 μL) were diluted with methanol (at least 20-fold), heated to 60° C. for 2 minutes to coagulate the enzyme, and centrifuged (10,000×g) for one minute). The supernatant (15 μL) was then injected.

Preparative Enzymatic Peptide Synthesis

In carbonate buffer (0.2 M, pH 9.1)/DMF (4:6, v/v), 50 mL, containing Z-L-Tyr-OMe (50 mM), D-amino acid methyl ester (100–800 mM), and 0.2 mM subtilisin was stirred at room temperature. The reaction was monitored by HPLC, and was stopped when maximum yield was obtained. The mixture was added to an equal volume of ice water. After filtration, the precipitate was washed with 1 N HCl, water, 0.2 M Na$_2$CO$_3$, and water, then recrystallized from ethanol/water. Typical yields were in the range of 70–80%.

NMR Analyses

Proton NMR spectra were obtained on a Varian EMS-390 (90 MHz) instrument. Samples were dissolved in DMSO-d$_6$, containing Me$_4$Si as the internal standard. $^{13}$C NMR spectra were taken on a Varian XL-200 instrument (50 MHz). Resonance assignment was aided by an attached proton test (APT) spectrum (Patt, S. L., *J. Magn. Reson.* 636 (1982). Methyls and methines have opposite sign from methylenes and quartenary carbons. The α-C (0.2–0.4 ppm) can be seen if racemization occurs.

Results of Chemical Peptide Synthesis Z-Phe-OCH$_2$CN 1 gram of Z-L-Phe-OH or Z-D-Phe-OH was dissolved in 2 mL of triethylamine and 2 mL of chloroacetonitrile. The reaction was stirred for two hours at room temperature. The reaction was concentrated under vacuum and the residue taken up in 5 mL ethyl acetate. The ethyl acetate was then washed with 2% Na$_2$CO$_3$ (3x), water (2x), 1 N HCl (2x), water (2x), and 0.5 M or higher saline (1x). The organic phase was dried over MgSO$_4$, and concentrated to dryness. The residue was recrystallized from CH$_2$Cl$_2$/hexanes. Yield for Z-L-Phe-OCH$_2$CN was 1.0 g (89%). M.P. 53°–55° C. $[\alpha]_d$(c 2, DMF)+6.6°. $^1$H-NMR (CDCl$_3$) 3.1 (d, 2H, Phe βH), 4.7 (m, 3H, αH and cyanomethyl), 5.1 (s, 2H, CBZ βH), 5.2 (d, 1H, amide), 7.3 (m, 10 H, Phe and CBZ phenyl). Z-D-Phe-OCH$_2$CH, yield 0.88 g (78%). M.P. 53°–54° C. $[\alpha]_d$ (c, 2, DMF)-6.1°.

Boc-L-Phe-OCH$_2$CN

Synthesis identical to Z-Phe-OCH$_2$CN. Yield 88%. M.P. 67°–68° C. $[\alpha]_D$ (c 2, DMF)+8.2. $^1$H-NMR (CDCl$_3$) 0.9 (s, 9H, Boc), 3.0 (m, 2H, Phe βH), 4.6 (m, 3H αH and cyanomethyl) 5.2 (d, 1H, amide), 7.2 (m, 5H, Phe phenyl).

L-Phe-OCH$_2$CN, HCl 0.5 g of BOC-L-Phe-OCH$_2$CN was dissolved in 0.5 mL of a solution of trifluoroacetic acid and anisole (9:1, v/v), under argon, and stirred for thirty minutes. The solvent was concentrated under vacuum, and 3 mL of 4N HCl/dioxane were added. The solvent was concentrated under vacuum, and anhydrous ether was added to affect crystallization. The solid was collected by filtration and washed with ether. The produce was homogenous by TLC (Rf 0.29), detection by ninhydrin and UV absorption. $[\alpha]_D$ (c 1, DMF) $-17.2$.

H-Gly-Gly-OMe 2.5 g (19 mmoles) of Gly-Gly-OH was suspended in 25 mL of dry methanol. Two equivalents of thionyl chloride were added, and the suspension stirred to dissolution. The mixture was allowed to sit at room temperature overnight. The solvent was removed under vacuum, the residue taken up in a minimum of methanol, and anhydrous ether added to effect crystallization. Yield 3.2 g (92%). M.P. 146°–146° C. $^1$H-NMR (DMSO) 3.6 (s, 3H OMe), 3.8 and 3.9 (d, 2H, Gly α-H's).

Z-Tyr-Gly-Gly-Ome 330 mg (1 mmole) of Z-L-Tyr-OMe, 400 mg (2.2 mmole) of H-Gly-Gly-Ome, HCl were suspended in 5 mL DMSO and 5 mL 0.1 M tris-HCl, pH 8.9. 25 mg of α-chymotrypsin were added and the reaction stirred for 30 minutes. Five volumes of ice water were added, and the precipitate collected by filtration. Yield 312 mg (70%, based on acyl-donor). Amino acid analysis: tyr$_{1.0}$,gly$_{2.1}$.

Z-L-Tyr-Gly-Gly-OH 0.5 g (1.1 mmole) of Z-L-Tyr-Gly-Gly-OMe was dissolved in 3 mL of methanol. Two equivalents of 4 N NaOH were added, and the reaction was stirred for 2 hours, at which time TLC revealed all the starting material had been consumed. (R$_f$:Z-Tyr-Gly-Gly-OMe, 0.76: Z-Tyr-Gly-Gly-OH, 0.32.) The pH was adjusted to neutrality with 6N HCl and the reaction concentrated under vacuum. 0.5 mL of water was added and the pH dropped to 2. This aqueous solution was washed (4x) with ethyl acetate and the combined ethyl acetate fractions were dried over MgSO$_4$, then concentrated under vacuum. The residue was crystallized from CH$_2$Cl$_2$/hexanes. Yield 450 mg (95%). M.P. 213°–214° C. (lit. 214°–215° C.). [α]$_D$ -23.9 (c 1.2, DMF). Amino acid analysis: tyr$_{1.0}$, gly$_{1.9}$.

Z-L-Tyr-Gly-Gly-Phe-OCH$_2$CN 300 mg (0.69 mmole) of Z-Tyr-Gly-Gly-OH was dissolved in 5 mL dry THR, and the temperature was lowered to −10° C. in a dry ice/ethylene glycol bath. One equivalent of N-methyl morpholine and 1 equivalent of isobutyl chloroformate was added with stirring. One equivalent of H-L-Phe-OCH$_2$CN, HCl (166 mg), and 1 equivalent of N-methyl morpholine dissolved in 2 mL DMF was added and the solution stirred for 5 minutes. The reaction was allowed to come to room temperature, then diluted with six volumes of ethyl acetate. The ethyl acetate was washed with cold water (2x), 0.1 N HCl (3x), 0.2 M Na$_2$CO$_3$ (2x), water (2x) and concentrated brine (1x). The ethyl acetate as concentrated carefully under vacuum, and the residue was recrystallized from CH$_2$Cl$_2$/hexanes to give 260 mg (62%) of Z-Tyr-Gly-Gly-Phe-OCH$_2$CN. Amino acid analysis: tyr$_{1.0}$, gly$_{1.9}$, phe$_{0.9}$.

H-Phe-L-Leu-NH$_2$, HCl 350 mg of Z-L-Phe-L-Leu-NH$_2$ was dissolved in 10 ml dry methanol and 0.1 mL of 3% methanolic HCl was added, along with 200 mg palladium on charcoal and placed in a pressure bottle. The bottle was purged with hydrogen and then placed under hydrogen at 20 psi, and stirred for two hours. The solution was filtered through celite and concentrated under vacuum. Addition of ether gave a while solid. Recrystallization from methanol/ether gave 200 mg of deprotected peptide. Amino acid analysis: Phe$_{1.0}$, Leu$_{0.9}$, TLC analysis: RF 0.21, ninhydrin positive, UV positive. $^1$H-NMR (DMSO) 0.75 (m, 6H, Leu φ-H), 1.1 (m, 1H, Leu λ-H), 1.4 (d, 2H, Leu β-H), 3.0 and 3.2 (dd, 2H, Phe β-H), 4.05 (m, 2H, Phe, Leu α-H), 7.2 (m, 5H, Phe phenyl).

Z-(leu) Enkephalinamide 2 mg of (leu)enkephalinamide acetate was dissolved in 0.05 mL of 5% NaHCO$_3$ and 0.02 mL dioxane. The solution was cooled to 0° C. and 2 equivalents of benzyl chloroformate were added. The solution was stirred for three hours, and the dioxane was removed under vacuum. The residue was extracted with hexanes (3x) to remove excess benzyl chloroformate and the precipitated product was collected by filtration, washed with 1 N HCl, water, 5% NaHCO$_3$, and water, and then dried under vacuum. No purification was performed. Alternate synthesis: 50 mg Z-Tyr-Gly-Gly-OH was coupled with H-Phe-Leu-NH$_2$ by the mixed anhydride method. The usual workup gave a product with the identical Rf (TLC) and retention time (HPLC) as the previous synthesis.

Results of Enzymatic Peptide Synthesis

For dipeptide syntheses, 100 mM acyl donor and 200 mM acyl acceptor were dissolved in 1 mL 0.1 M Tris/HCl, pH 8.9/DMF (1:1, v/v). Quickly, 1.2 mg of the appropriate enzyme was added, and the reaction was stirred. At various times, 10 1μl aliquots were removed, dissolved in 4 volumes of methanol to quench the reaction, centrifuged at 13,000 g for 2 minutes to remove denatured enzyme, and analyzed by reverse phase HPLC.

For the pentapeptide syntheses these reaction conditions were found to produce only slow acyl donor hydrolysis and little peptide. For these reactions 0.1 M phosphate/35% dioxane or acetonitrile (pH 10) was used.

N-protected peptide esters can be prepared chemically based on oxime-resin method (Kaiser, E. T. Angew. Chem. Int. Ed. Engl. 27, 913 (1988)) and used in the enzymatic fragment coupling under the conditions where the amidase activity is suppressed. The results are shown in Tables 4 and 5.

TABLE 4

Physical Data of the Peptides Prepared in Subtilisin-Catalyzed Syntheses.[a]

| Product | Yield %[b] | mp °C. | [α]$_D$ deg (c 1, CHCl$_3$) | R$_f$[c] |
|---|---|---|---|---|
| Z—L—Tyr—D—Met—OMe | 80 | 143–144 | +18.1 | 0.28 (I) |
| Z—L—Tyr—D—Ser—OMe | 72 | 164–165 | −9.2 | 0.37 (I) |
| Z—L—Tyr—D—Phe—OMe | 75 | 170–173 | +8.1 | 0.48 (I) |
| Z—L—Tyr—D—Arg—OMe | 50 | 120–124 | +10.1 | 0.14 (II) |
| Z—L—Tyr—L—Arg—OMe | 71 | 118–121 | −7.3 | 0.14 (II) |
| Z—L—Tyr—D—Leu—OMe | 74 | 114–116 | +12.1 | 0.48 (I) |
| Z—L—Tyr—L—Val—OMe | 20 | 143–145[d] | −11.1[d] | 0.53 (I) |
| Z—L—Tyr—D—Val—OMe | 20 | 118–119 | +5.2 | 0.53 (I) |
| Z—L—Phe—D—Met—OMe | 76 | 191–193 | +10.0 | 0.50 (I) |
| Z—L—Phe—D—Ala—OMe | 57 | 125–126 | +11.3 | 0.60 (II) |
| Z—L—Phe—D—Val—NH$_2$ | 80 | 125–127 | +17.6 | 0.58 (I) |

[a]Conditions: 50 mM acyl donor, 800 mM acyl acceptor, 0.2 mM enzyme, 0.2M carbonate (pH 9.1 prior to addition of cosolvent)/50% DMF, 25° C.; total volume 50 mL. Reaction was stopped when no donor ester was detected (5–15 min.) The physical constants of the products are in agreement with those prepared chemically.
[b]Determined by HPLC before isolation.
[c]Solvents for TLC on silica gel plates: (I) CHCl$_3$/EtOAc (7:3, v:v); (II) CHCl$_3$/MeOH (9:1, v:v).
[d]The literature values are 144–147° C. and −11.7° C. respectively (Schroder, E., Justus Liebigs Ann. Chem. 680: 142 (1964)).

TABLE 6

Subtilisin Catalyzed Peptide Synthesis.[a]

| # | Acyl Donor | Acyl Acceptor | RXN Time | Yield |
|---|---|---|---|---|
| 1 | Z—L—Phe—OCH$_2$CN | L—Leu—NH$_2$ | 10 Min | 88 |
| 2 | Z—L—Phe—OCH$_2$CN | D—Leu—OMe | 30 Min | 68 |
| 3 | Z—L—Leu—OCH$_2$CN | L—Leu—NH$_2$ | 30 Min | 77 |
| 4 | Z—Y—G—G—F—OCH$_2$CN | L—Leu—NH$_2$ | 40 Min | 99 |
| 5 | Boc—L—Cys(SBzl)—OMe | D—Val—OBzl | 4 Hours | 70 |
| 6 | Pha—L—Cys(SAcm)—OMe | D—Val—OMe | 4 Hours | 72 |

[a]Reaction conditions unless otherwise indicated. 100 mM acyl donor. 200 mM acyl acceptor, 1-2 mg enzyme, in 1 mL 0.1M Tris. HCl/DMF (1:1). pH 8.8. Pha, phenylacetyl.

Now having fully described this invention, it will be understood by those with skill in the art that the invention may be performed within a wide and equivalent range of conditions, parameters, and the like, without affecting the spirit or scope of the invention or any embodiment thereof.

What is claimed is:

1. A method for the formation of a 5'-acylnucleoside, comprising condensing an enol ester with the sugar residue of a nucleoside in a reaction medium comprising an organic solvent, wherein the reaction is catalyzed by subtilisin mutein 8350 which is stable relative to native subtilisin in said reaction medium.

2. The method of claim 1, wherein said nucleoside is deoxyadenosine, adenosine, deoxyinosine, inosine. deoxycytidine, cytidine, 2'-azido-2'-deoxycytidine, thymidine, 3'azido-3'-deoxythymidine, deoxyguanosine, guanosine, uridine, 2'-azido-2'-deoxyuridine or pseudouridine.

3. The method of claim 1, wherein said reaction medium is anhydrous DMF.

* * * * *